United States Patent [19]

Hayden

[11] Patent Number: 4,837,194

[45] Date of Patent: Jun. 6, 1989

[54] PROCESS FOR IMPROVING THE PERFORMANCE OF A CATALYST FOR THE PRODUCTION OF ALKYLENE OXIDES

[75] Inventor: Percy Hayden, Guisborough, England

[73] Assignee: Imperial Chemical Industries PLC, London, England

[21] Appl. No.: 144,107

[22] Filed: Jan. 15, 1988

Related U.S. Application Data

[63] Continuation-in-part of Ser. No. 883,763, Jul. 9, 1986, abandoned.

[30] Foreign Application Priority Data

Jul. 31, 1985 [GB] United Kingdom ............... 8519223
Jun. 6, 1986 [GB] United Kingdom ............... 8613818

[51] Int. Cl.$^4$ .................. B01J 21/04; B01J 23/04; B01J 23/50
[52] U.S. Cl. ................................ 502/348; 549/534
[58] Field of Search ............................. 502/347, 348

[56] References Cited

U.S. PATENT DOCUMENTS

| | | | |
|---|---|---|---|
| 4,033,903 | 7/1977 | Maxwell | 502/347 |
| 4,186,106 | 1/1980 | Rebsdat et al. | 252/414 |
| 4,207,210 | 6/1980 | Kilty | 252/463 |
| 4,406,820 | 9/1983 | Busse | 502/347 X |
| 4,419,276 | 12/1983 | Bhasin et al. | 502/347 |

FOREIGN PATENT DOCUMENTS

| | | |
|---|---|---|
| 0001078 | 3/1979 | European Pat. Off. |
| 0085237 | 8/1983 | European Pat. Off. |
| 2103508 | 2/1983 | United Kingdom |

OTHER PUBLICATIONS

Alkalidotierung bei Heterogenkatalysatoren (pp. 31–32 translated) Dr. Wolf Dieter Mross, BMFT-FB-T 83–174.

*Primary Examiner*—W. J. Shine
*Attorney, Agent, or Firm*—Cushman, Darby & Cushman

[57] ABSTRACT

The performance of a catalyst for the oxidation of alkenes to alkylene oxides which comprises silver on alpha alumina is improved by introducing an alkali metal selected from lithium, sodium, rubidium and/or potassium to the catalyst in a ratio of one part chemically absorbed to at most three parts physically absorbed by impregnation with a solution of an alkali metal compound in a solvent which has dielectric constant of at most 8.

8 Claims, No Drawings

PROCESS FOR IMPROVING THE PERFORMANCE OF A CATALYST FOR THE PRODUCTION OF ALKYLENE OXIDES

This application is a continuation-in-part of Application Serial No. 883,763, filed July 9, 1986, now abandoned.

This invention relates to catalysts for the production of alkylene oxides, for example propylene oxide and preferably ethylene oxide.

Catalysts for the production of olefin oxides, for example ethylene oxide by the oxidation of olefines normally comprise silver supported on a heat resisting support. The catalyst supports normally comprise particles of alpha alumina which are fused and/or bonded by cements to form porous pellets into which the silver is introduced for exmaple by impregnation of the support with a solution of a decomposable silver compound, drying and decomposing the silver compound to silver.

We believe that the portions of the support surface which are not covered with silver may possess a catalytic activity which contributes to the total oxidation of the olefine and/or olefine oxide to carbon dioxide and water; for example they may isomerise ethylene oxide to acetaldehyde which is then subject to further oxidation.

It has been proposed to promote the catalysts by the addition of alkali metals, especially cesium and /or rubidium, to them. This has been carried out by impregnating the catalyst or its support before, during or after the introduction of the silver with a solution comprising the alkali metal, the alkali metal being deposited by evaporating the solution. The alkali metal is believed to be present in such catalysts largely in the form of a physical deposit.

In our European patent application Ser. No. 85237 we disclosed that improved catalysts may be obtained by chemically absorbing cesium and/or rubidium on to the surface in a concentration of at least 0.003 and preferably at least 0.008 gram equivalents per kilogram of the element based on the total weight of the catalyst and preferably in an amount equivalent to at least 0.003 gram equivalents of the element per kilogram based on the total weight of the catalyst per square metre per gram of support surface area.

We have now found an improved procedure enables an alkali metal promoter to be introduced in a particularly desirable form.

This invention comprises a process for improving the performance of a catalyst for the production of alkylene oxides for example propylene and preferably ethylene oxide by the reaction of the corresponding alkene with oxygen, which comprises silver supported on an α-alumina support which comprises introducing an alkali metal selected from lithium, sodium, rubidium, and/or preferably potassium to the catalyst in a ratio of one part chemically absorbed (absorbed) to at most three preferably at most two and more preferably at most one part physically deposited, by contacting the catalyst with a solution or colloidal solution of a compound of lithium, sodium, rubidium, and/or preferably potassium in a solvent which has a dielectric constant of at most 8 and preferably at most 5 at 20° C. The solvent may be a hydrocarbon, suitably boiling in the range 50° to 250° C. at atmospheric pressure for example benzene or alkyl benzenes for example toluene or an aliphatic hydrocarbon and need not be a single compound, hydrocarbon mixtures and especially substantially aliphatic hydrocarbon mixtures preferably boiling in the range 50° to 250° C. at atmospheric pressure being preferred. If desired small quantities of for example at most 10% and preferably at most 5% by weight of alcohols, polyethers or acids preferably having at least 5 and suitably at most 20 carbon atoms per —OH group may be incorporated to assist solubility of the alkali metal compound.

The alkali metal compound is suitably a salt of a carboxylic acid preferably having at least 5 for example 5 to 20 and more preferably 7 to 12 carbon atoms per —COOH group. Suitable salts are for example octanoates such as 2-ethyl hexanoates.

By "colloidal solution" is meant to diperison which produces a precipitation of at most 10% of the dispersed phase in the course of one day. The catalyst may be contacted with a solution or colloidal solution one or more times. Furthermore the whole process of alkali deposition i.e. impregnantion and drying may be repeated to reach the preferred level and type of alkali metal content in the catalyst.

The catalyst suitably comprises at least 0.001 gram equivalents and preferably at least 0.002 gram equivalents and preferably at most 0.03 and more preferably at most 0.015 gram equivalents of the alkali metal chemically absorbed on the surface of the support per kilogram of the total catalyst. The amount of the alkali metal chemically absorbed is suitably in the range 50 to 1000 and preferably 60 to 250 parts per million per square metre per gram of support surface area. By parts per million is meant parts per million by weight potassium, lithium, sodium and/or rubidium expressed as the element based on the total weight of the catalyst.

The quantity of chemically absorbed alkali metal may be determined as follows. The catalyst may be impregnated with a solution comprising the alkali metal compound drained and dried and analysed for the alkali metal. The amount of the alkali metal deposited in the catlayst as a mere result of evaporation of the solution may be calculated from the concentration of the alkali metal compound in the residual solution and the porosity of the catalyst. This gives the alkali metal content of the solution contained in the pores of the catalyst and which is incorporated in the catalyst as physcially held alkali metal salt deposited by evaporation of the solution. The excess alkali analysed to be in or on the catalyst over and above this figure is the chemically absorbed alkali metal. An alternative method of determining the chemically absorbed alkali metal is to wash the catalyst with the impregnating solvent, which removes only physically held alkali metal and then water which removes the more strongly held chemically absorbed alkali metal. The quantity of alkali metal removed in the second step is that which had been chemically absorbed. A further alternative method is to measure the depletion of alkali metal compound from the impregnating solution which, together with knowledge of the volume of the impregnating solution enables an evaluation of the more strongly held chemically absorbed alkali metal to be made.

The quantity of chemically absorbed alkali metal may be increased by the following means.

(1) Prolonged exposure of the catalyst and/or support to the impregnating solution tends to produce an increase in the level of chemically absorbed alkali metal. Typically impregnantion should be continued for at least 4 preferably at least 8 and more preferably at least 16 hours at temperatures of 15° to 60° C. and preferably at least one hour and more preferably at least four hours at temperatures above 60° C.

(2) In order to increase the number of sites available for potassium, lithium, sodium and/or rubidium absorption the surface of the support is preferably cleaned from contaminants before the potassium, lithium, sodium and/or rubidium is introduced. If ionic or basic material, for example amines left on the catalyst from a silver impregnation and decomposition process or physically deposited alkali metal compounds is present, it may be at least partly removed by washing with a suitable solvent, for example water. If organic material is deposited in the catalyst and impedes chemical absorption of the potassium, lithium, sodium and/or rubidium it may be removed by oxidation for example with oxygen at elevated temperatures for example 200° to 300° C.

The process is suitably carried out at a temperature in the range 10° C. to 200° C., for example 20–50° C. and preferably 30–100° C.

The weakly held alkali metal compound may be selectively or partially selectively removed by washing of the alkali metal impregnated catalyst with a solvent having a dielectric constant in the range 5 to 35 and preferably 10 to 30.

The $\alpha$-alumina support preferably has a specific surface area in the range 0.05 to 10 $m^2/g$ and preferably 0.1 to 5 $m^2/g$ and more preferably 0.3 to 2$m^2/g$ as measured by the Brunauer Emmett and Teller method.

The catalyst support preferably has an apparent porosity as measured by the mercury absorption method of at least 20%, for example 25–80% preferably 25–60% and more preferably 45–60% and mean pore diameters of 0.1 to 20 microns preferably 0.2 to 2 microns as measured by the mercury porosimetry method.

Silver may be introduced to a pre-formed porous heat resisting support as a suspension of silver or silver oxide in a liquid medium for example water or by impregnation of the support with a solution of a silver compound which can be reduced to silver metal if necessary by means of a reducing agent for example hydrogen. If necessary a heat treatment may be used to decompose the silver compound to silver. Suitably the impregnating solution contains a reducing agent which may be for example an anion, for exmaple a formate, acetate, propionate, lactate, tartarate or preferably oxalate ion, of a silver compound in the solution. The reducing agent may be for example an aldehyde, for example formaldehyde or acetaldehyde or an alcohol preferably having 1 to 4 carbon atoms for example methanol or ethanol.

The solution of the silver compound may be a solution in water and/or an organic solvent, for example in aliphatic alcohol preferably having 1 to 4 carbon atoms, a polyhydric alcohol for example ethylene glycol or glycerol, a ketone for example acetone, an ether for example dioxan or tetrahydrofuran, a carboxylic acid for example acetic acid, or molt latic acid which is preferably used in the presence of water, or an ester for example ethyl acetate or a nitrogen containing base for example pyridine or formamide. An organic solvent may function as a reducing agent and/or complexing agent for the silver also.

If the silver is introduced by impregnating a support with a solution of a decomposable silver compound it is preferred that ammonia and/or a nitrogen containing base should be present. The nitrogen containing base suitably acts as a ligand maintaining the silver in solution; for exmaple it may be pyridine, acetonitrile, an amine, especially a primary or secondary amine having 1–6 carbon atoms, or preferably ammonia. Other suitable nitrogen-containing bases include acrylonitrile, hydroxylamine and alkanolamines for example ethanolamine, alkylene diamines having from 2–4 carbon atoms or amides for example formamide or dimethyl formamide. The nitrogen-containing bases may be used alone or in admixture, mixtures of ammonia and a second nitrogen containing base being preferred. Suitably the nitrogen containing base or bases are used together with water. Very suitably the solution comprises silver nitrate and a lower alkyl amine having 1 to 5 carbon atoms, for example isopropylamine, in water.

Alternatively the solution may be a neutral or acid solution for example it may be a solution of a silver carboxylate especially a formate, acetate, propionate, oxalate, citrate, tartarate or preferably lactate or for example a solution of silver nitrate.

The solutions preferably contain 3–50% of silver by weight.

Impregnation may be carried out in a single stage or if desired may be repeated one or more times. By this means higher silver contents of the catalyst may be achieved.

The silver compound may generally be reduced to silver by heating in the range 100 to 350° C., for example for a period of 15 mins to 24 hours, preferably in the substantial absence of oxygen, for example in the presence of an inert gas for example nitrogen.

Most of the silver content of the catalyst is preferably present in the form of discrete particles adhering to the support having equivalent diameters of less than 10,000Å preferably in the range 20–10,000Å and more preferably 40–8,000Å. By equivalent diameter is meant the diameter of a sphere of the same silver content as the particle.

Preferably at least 80% of the silver is present as particles having equivalent diameters ifn the aforesaid range, the quantity of silver being judged in terms of the number of particles falling in that range. The silver may be present as silver and/or silver oxide and is thought to be present normally as silver particles having a surface layer of silver oxide. The dimensions of the silver particles may be determined by scanning electron miscroscopy.

The catalyst preferably comprises 3 to 50% and more preferably 5 to 15% by weight of silver.

Any alkali metals present as components of the support in non water extractable form are ignored as they do not contribute to catalysis.

The invention also provides processes for the production of alkylene oxides for example ethylene and propylene oxides by the oxidation of the corresponding olefine with oxygen using a catalyst as aforesaid.

Partial pressures of ethylene or propylene in such processes may be in the range 0.1–30 and preferably 1 to 30 bars. The total pressure may be in the range of from 1 to 100 and preferably 3–100 bars absolute. The molar ratio of oxygen to ethylene or propylene may be in the range 0.05 to 100. The partial pressure of oxygen may be in the range 0.01 and preferably 0.1 to 20 bars and preferably 1–10 bars. The oxygen may be supplied for example in the form of air or preferably as commercial oxygen. A diluent for example helium, nitrogen, argon and/or carbon dioxide and/or preferably methane may be present in proportions of 10–80% and preferably 40–70% by volume in total. Ethane may also be present preferably in the range 0.1–5% by volume. It is necessary to operate using gas compositions which are outside the explosive limits.

The temperature is suitably in the range 200–300° C., and preferably in the range 210–290° C. Contact times should be sufficient to convert 0.1–70%, for example 2 to 20 and preferably 5–20% of the ethylene or propylene and unconverted ehtylene or propylene is suitably recycled.

A reaction modifier is suitably present. Suitable reaction modifiers comprise chlorine and may be for example chlorinated alkenes having 1–6 carbon atoms for example methyl chloride or teriary butyl chloride, dichloromethane or chloroform, a chlorinated biphenyl or polypenyl, a chlorinated benzene which may be for example monochlorobenzene or especially vinyl chloride or ethylene dichloride. The concentration of the reaction modifier depends on its chemical nature of example in the case of ethylene dichloride 0.02 to 10 and preferably 0.05–5 parts per million by weight are normally present and in the case of vinyl chloride 0.05–20 and preferably 0.1–10 parts per million by weight are suitably present.

We have found that with appropriate concentrations of such reaction modifiers, especially vinyl chloride, attractive selectivities may be secured.

It is preferred that a substance be present in the gas phase which is an oxide of nitrogen, espeically NO, $NO_2$ or $N_2O_4$ or which is capable of being oxidised to such an oxide of nitrogen under the reaction conditions, or is capable of introducing nitrate and/or nitrite ions to the catalyst under the reaction conditions. Such a process may suitably be carried out as described in our UK Pat. No. 2,014,133.

The dielectric constants refer to those measured at low frequencies at 20° C.

EXAMPLES 1–8

Preparation of the catalysts

Catalyst support pellets, comprising porous, high purity α-alumina containing 250±50 ppm of silicates expressed as silicon and 40±10 ppm sodium compounds expressed as sodium, in the form of cylinders 8 mm diameter and 8 mm long pierced by seven longitudinal holes 1.22 mm in diameter one being central and the others being regularly spaced on a circle of 4.39 mm diameter centred on the axis of the pellet were uniformly coated with silver metal particles as described below. The mean pore diameter of the porous alumina was 2.4 microns, its water porosity was 0.31 ml per g and its surface area was 0.52 m² per g.

Silver nitrate (4,418 g) was dissolved at 70° C. into distilled water (896 ml) and the resulting solution cooled to 50° C. Monoisopropylamine (4,800 ml) was slowly added to this solution whilst stirring and cooling. The addition of the amine was sufficiently slow to avoid undue temperature rises causes by the exothermic process of complex formation between the amine and the silver salt. The temperature was maintained in the range 40 to 60° C. The resulting clear solution was cooled to room temperature.

Support pellets (4,200 g) were evacuated before the addition of the solution of silver nitrate/monoisopropylamine complex (5,000 mls). After contracting the solution for 30 minutes, the impregnated pellets were separated from the residual solution and drained.

The support pellets, wet with the impregnated complex solution, were charged to a perforated basket which was then loaded into a reactor. The impregnated support was heated in a stream of hot nitrogen gas, the temperature of the reactor being set at 100° C. and subsequently gradually increased from 100° C. to 300° C. over a period of 18 hours. The impregnated complex decomposed to leave particulate silver evenly dispersed on the surface of the porous α-alumina pellets. The pellets also contained a residue of substances containing carbon and nitrogen.

The silver-coated pellets were subsequently contacted with hot air in a process which began by passing a steam of 5% air-in-nitrogen over the pellets heated at 150° C. Subsequently the air content of the gas stream and the reactor temperature were both gradually increased to 100% and 300° C., respectively. The rate of both changes were sufficiently slow as toa void uncontrolled rises in temperature of the pellets due to the exothermicity of the process. On reaching 300° C., the pellets were contacted with the air-stream for a further 14 hours and then allowed to cool.

The resulting silver-coated pellets, now substantially free of the residues of the anaerobic decomposition process were contacted with hot water in the temperature range 90 to 100° C. for 16 hours, then cooled, drained and dried by contacting with a stream of hot nitrogen. The product was a catalyst percursor and was characterised as a substantially clean, dry dispersion of silver particles evenly coated on the surfaces, both internal and external, of the porous α-alumina pellets.

EXAMPLE 1

The catalyst precursor (154 g; water absorption, 0.24 ml per g; methanol absorption, 0.24 ml per g; white spirit absorption, 0.24 ml per g) was impregnated with a solution (184.8 ml) of potassium 2-ethyl hexanoate (341 grams of potassium per one million ml of solution) dissolved in a solvent comprising 0.4% of 2-ethyl hexanol mixed with White Spirit (British Standard Specification B.S. 245:1956). The catalyst precursor was contacted with the potassium solution for 16 hrs, after which the pellets were separated from the residual solution, drained and dried. The residual solution contained 276 grams of potassium per one million ml of solution (ppm, w/v) whilst the dried potassium-doped catalyst contained 137 ppm, w/w of potassium as extractable into dilute aqueous hydrochloric acid. As evaluated from the water absorbency and the concentration of the potassium solution originally added to the pellets (i.e. the unused solution), the catalyst would have been expected to contain 82 ppm w/w of potassium.

The actual level of potassium on the catalyst was thus 67% in excess of the expected level.

As evaluated from the concentration of potassium in the final solution contacting the catalyst pellets, the amount of potassium deemed to have been physically deposited (absorbed) into the porous pellets is 66 parts of potassium per million parts of dry catslyst, w/w. Furthermore, the depletion of 65 ppm w/v of potassium from the solution during the impregnation process is deemed to have been the consequence of a process of chemical absorption (absorption) of 78 parts of potassium per million parts of catalyst. Thus together, the processes of absorption of the solution and adsorption of the solute are deemed to have deposited a total of 144 ppm of potassium on the catalyst, the difference from the 137 ppm aforesaid being within the limits of analytical accuracy.

The potassium-doped catalyst (5 g) was crushed and sieved to produce particulate matter in the size range 450 to 1000 microns (3 g). An aliquot (0.4 g) of the particulate matter was loaded into a middle sector of a stainless steel reactor (length, 24.4 cm; internal diameter 2 mm). The catalyst (length, 8 cm) was located in the reactor between glass beads and glass-wool plugs.

A gas mixture of ethylene (30%) oxygen (8%) carbon dioxide (1.1%), ethane (0.3%), vinyl chloride (8 ppm), ethyl chloride (2 ppm) and 2-nitropropane (20 ppm) with nitrogen to balance was passed at a pressure of 16 atmospheres absolute over the catalyst. The gas was passed at a space velocity of 3600 hr $^{-1}$ for a standard period of time. This method of of testing was used throughout examples 1 to 8.

The reaction produced ethylene oxide and also some total combustion of ethylene to carbon dioxide and water.

The temperature of the reactor was adjusted to achieve 30% conversion of the oxygen fed. The latter temperature is designated $T_{30}$ and was measured to be 245° C. It is a measure of the activity of the catalyst. The selectively of the catalyst, S, is the number of moles of ethylene oxide produced expressed as a percentage of the number of moles of ethylene consumed. $S_{30}$ is the selectivity at 30% conversion of oxygen and was observed to be 84.3%.

The conversion of oxygen was found to fall gradually through the test. To maintian 30% conversion of oxygen, the reactor temperature had to be gradually increased throughout the test; through the test, the overall increase in $T_{30}$ was 3° C.

EXAMPLE 2

Catalyst 2 was prepared by impregnation of a further aliquot of the silvered pellets used in the preparation of catalyst 1. Under the same method of testing as catalyst 1, its starting $S_{30}$ was 83%, its starting $T_{30}$ was 240° C. and temperature of the reactor needed to be increased by 2° C. in the course of the test.

EXAMPLE 3

Catalyst 3 was prepared by the procedure used in Example 1 excepting that the potassium impregnation was performed on a smaller scale.

Catalyst A was prepared by a method not according to the invention using potassium formate dissolved in methanol. By experiment, the concentration of potassium in the impregnating liquid was selected at a level such that the starting $S_{30}$ and starting $T_{30}$ of catalyst A was as near as was practicable to those achieved by catalyst 3 under the test procedure of Example 1.

Catalyst 3 required its temperature to be increased by 4° C. to maintain oxygen conversion at 30% whereas catalyst A required its temperature to be increased by 9° C. over the same period of time in both cases under the test procedure of Example 1.

EXAMPLE 4

Catalyst 4 was prepared using a larger excess volume of impregnating solution (11.1 ml) over that required merely to fill the porous volume of the silvered pellets (1.06 ml) than had been the case in the preparation of catalyst 3. By experiment with different concentrations of potassium 2-ethyl hexanoate, one was found that enabled the catalyst to reproduce closely the performance of catalyst 3. The Table shows that the concentration of potassium in the original impregnating solution was very much lower for catalyst 4 than was the case for catalyst 3.

Catalyst 5 was prepared using the same large excess volume of impregnating solution relative to that required to fill the porous volume contained in the pellet; the ratio was 10.4. However catalyst 5 was prepared from a solution containing a higher concentration of potassium than was used for catalyst 4. Although an improved selectivity of ethylene oxide synthesis was achieved, the activity of the catalyst diminished through the test rather more than was the case with catalyst 4.

Catalysts B and C were prepared from solutions of potassium formate in menthol. By experiment the concentration of potassium formate used in the preparation of catalyst B was that which enabled the starting performance of the catalyst to equal that of catalyst 4. When tested as for catalyst 1, the activity of catalyst B fell by an amount requiring the operating temperature of catalyst B to be increased by 50° C. whereas over the same period the operating temperature of catalyst 4 was required to be increased by only 3° C.

Catalyst C was prepared by methods similar to those applied to catalyst B excepting that by experiment the level of potassium was selected such that the fall in catalyst activity during the test procedure caused the operating temperature to be increased by 19° C., an increase equal to that necessary over the same period of time to maintain the oxygen conversion over catalyst 5. It will be noted that the selectivity achieved by catalyst 5 is 1.7% higher than that of catalyst C. All test procedures for the catalysts were in accordance with that of Example 1.

EXAMPLE 5

As with Example 4, the concentrations of potassium carbonate in methanol used in the preparation of catalysts D and E permit comparisons with catalysts 4 and 5. The results show a preference for catalysts doped with potassium provided from potassium 2-ethyl hexanoate dissolved in a dilute solution of 2-ethyl hexanol in White Spirit.

EXAMPLE 6

Catalysts 6 and 7 were made from potassium 2-ethyl hexanoate dissolved in a solution of 0.05% 2-ethyl hexanol in White Spirit. The catalysts were tested as in Example 1 for the same period of time.

EXAMPLE 7

Catalysts 8 and F were made from potassium 2-ethyl hexanoate dissolved in a solution of 0.4% 2-ethyl hexanol in White Spirit and in methanol respectively.

EXAMPLE 8

Catalysts 9 and 10 were made from potassium 2-ethyl hexanol in toluene.

The result of Examples 1 to 8 are tabulated. In all of the above Examples the catalysts were tested for selectivity in accordance with the procedure of Example 1.

| KEY FOR TABLE 1 | |
|---|---|
| Potassium solute | Potassium compound |
| 1 | Potassium 2-ethyl hexanoate |
| 2 | Potassium formate |
| 3 | Potassium carbonate |
| Solvent Composition (by volume) | |
| I | 0.4% 2-ethyl hexanol in White Spirit |
| II | Methanol |

-continued

| KEY FOR TABLE 1 | |
|---|---|
| Potassium solute | Potassium compound |
| III | 0.05% 2-ethyl hexanol in White Spirit |
| IV | 0.4% 2-ethyl hexanol in Toluene | ppm means parts per million of the element by weight based on the total catalyst
w/w means by weight.

the silver salt. The temperature was maintained in the range 40 to 60° C. The resulting clear solution was cooled to room temperature.

Support pellets (4,200 g) were evacuated before the addition of the solution of silver nitrate/monoisopropylamine complex (5,000 mls). After contacting the solution for 30 minutes, the impregnated pellets were separated from the residual solution and drained.

The support pellets, wet with the impregnated com-

TABLE 1

| CATALYST | CATALYST WEIGHT g | VOLUME OF IMPREGNATING SOLUTION ML | CONCENTRATION OF POTASSIUM IN SOLUTION ppm, w/v | | CONCENTRATION OF POTASSIUM ON CATALYST ppm, w/w | | | |
|---|---|---|---|---|---|---|---|---|
| | | | Unused Solution | Used Solution | Expected | Absorbed | Adsorbed | Observed |
| 1 | 154 | 185 | 341 | 276 | 82 | 66 | 78 | 137 |
| 2 | 147 | 179 | 241 | 136 | 58 | 33 | 126 | 113 |
| 3 | 4.48 | 5.4 | 230 | | 55 | | | |
| A | 5.05 | 3.03 | 833 | | 200 | | | |
| 4 | 4.43 | 11.1 | 80 | | 19 | | | |
| 5 | 4.31 | 10.8 | 104 | | 25 | | | |
| B | 4.65 | 11.6 | 794 | 777 | 190 | 194 | 42 | 200 |
| C | 4.88 | 12.2 | 1000 | | 240 | | | |
| D | 4.49 | 11.2 | 600 | | 150 | | | |
| E | 4.74 | 11.9 | 691 | 671 | 166 | 168 | 50 | |
| 6 | 4.17 | 5.03 | 408 | 312 | 98 | 75 | 116 | 151 |
| 7 | 4.05 | 4.95 | 500 | 370 | 120 | 89 | 156 | 171 |
| 8 | 4.48 | 5.38 | 312 | | 75 | | | |
| F | 4.42 | 5.30 | 312 | | 75 | | | |
| 9 | 4.11 | 5.00 | 245 | | 59 | | | |
| 10 | 8.48 | 10.18 | 402 | 305 | 96 | 73 | 116 | |

| CATALYST | EXCESS OF OBSERVED OVER EXPECTED % | POTASSIUM SOLUTE | SOLVENT | $S_{30}$ | $T_{30}$ | Increase in $T_{30}$ °C. During Test |
|---|---|---|---|---|---|---|
| 1 | 67 | 1 | I | 84.3 | 245 | 3 |
| 2 | 95 | 1 | I | 83.0 | 240 | 2 |
| 3 | | 1 | I | 84.5 | 247 | 4 |
| A | | 2 | II | 84.3 | 246 | 9 |
| 4 | | 1 | I | 84.4 | 246 | 3 |
| 5 | | 1 | I | 86.8 | 247 | 19 |
| B | 5 | 2 | II | 84.4 | 246 | 15 |
| C | | 2 | II | 85.1 | 245 | 19 |
| D | | 3 | II | 84.6 | 243 | 15 |
| E | | 3 | II | 85.6 | 246 | 19 |
| 6 | 54 | 1 | III | 83.7 | 245 | 2 |
| 7 | 43 | 1 | III | 85.0 | 245 | 5 |
| 8 | | 1 | I | 83.1 | 239 | 3 |
| F | | 1 | II | 77.7 | 245 | 2 |
| 9 | | | IV | 84.5 | 243 | 3 |
| 10 | | 1 | IV | 85.2 | 245 | 3 |

Example 9

In this example, catalyst support pellets comprising α-alumina containing 460 ppm w/w compounds of silicon expressed as silicon, 88 ppm w/w sodium compounds expressed as sodium, 19 ppm w/w potassium compounds expressed as potassium, 360 ppm w/w iron compounds expressed as iron and 375 ppm w/w of calcium compounds expressed as calcium in the form of cylinders 8mm diameter and 7–9 mm long pierced by a single hole 2–3 mm diameter were used. The mean pore diameter of the porous alumina was 1.6 microns, its water porosity was 0.42 mols per g and its surface area was 0.72 m² per g. The pellets were uniformly coated with silver metal particles as described below.

Silver nitrate (4,418 g) was dissolved at 70° C. into distilled water (896 ml) and the resulting solution cooled to 50° C. Monoisopropylamine (4,800 ml) was slowly added to this solution whilst stirring and cooling. The addition of the amine was sufficiently slow to avoid undue temperature rises causes by the exothermic process of complex formation between the amine and plex solution, were charged to a perforated basket which was then loaded into a reactor. The impregnated supported was heated in a stream of hot nitrogen gas, the temperature of the reactor being set at 100° C. and subsequently gradually increased from 100° C. to 300° C. over a period of 18 hours. The impregnated complex decomposed to leave particulate silver evenly dispersed on the surface of the porousα-alumina pellets. The pellets also contained a residue of substances containing carbon and nitrogen.

The silver-coated pellets were contacted with hot water in the temperature range 90 to 100° C. for 16 hours, cooled, drained and dried in a stream of hot water in the temperature range 90 to 100° C. for 16 hours, cooled, drained and dried in a stream of hot nitrogen.

The washed silver-coated pellets were subsequently contacted with hot air in a process which began by passing a stream of 5% air-in-nitrogen over the pellets heated at 150° C. Subsequently the air content of the gas stream and the reactor temperature were both gradually increased to 100% and 300° C., respectively. The rate of both changes were sufficiently slow, as to avoid uncontrolled rises in temperature of the pellets due to the exothermicity of the process. On reaching 300° C., the pellets were contacted with the air-stream for a further 14 hours and then allowed to cool.

The resulting silver-coated pellets, now substantially free of the residues of the anaerobic decomposition process were again contacted with hot water in the temperature range 90 to 100° C. for 16 hours, then cooled, drained and dried by contacting with a stream of hot nitrogen. The product was a catalyst precursor and was characterised as a substantially clean, dry dispersion of silver particles evenly coated on the surfaces, both internal and external, of the porous60 -alumina pellets.

Portions of the catalyst precursor (water absorption, 0.33 ml per g; White Spirit absorption, 0.34 ml per g) were impregnated with various solutions of potassium carboxylates dissolved in a solvent comprising 1.3% v/v 2-ethyl hexanol mixed with White Spirit. The catalyst precursor was contacted with the potassium solution for 16 hrs, after which the pellets were separated from the residual solution, drained and dried.

Catalyst 11 was prepared by contacting the catalyst precursor (14.45g) with potassium 2-ethyl hexanoate (23.8 mls; 160 ppm w/v % potassium). As evaluated from the absorbency and the concentration of the potassium solution originally added to the pellets, the catalyst would have been expected to contain 54 ppm w/w of potassium. Catalyst 12 was prepared in a similar manner to catalyst 11 with the exception that the potassium solution contained 320 ppm w/v of potassium and accordingly catalyst 12 would have been expected to contain 108 ppm w/w of potassium.

Catalysts 13 and 14 were similar to catalysts 11 and 12, respectively, but different in that the potassium added was potassium neodecanoate.

ppm w/v prefers to grams of potassium per million ml of solvent.

Catalysts 11, 12, 13 and 14 were tested as in Example 1 with the exception that the carbon dioxide was replaced by additional nitrogen and that the gases were passed at a space velocity of 7200 hr $^{-1}$. The average results for catalysts 11 to 14 at from 3 to 8 days testing are tabulated below.

TABLE 2

| Catalyst | $S_{30}$ | $T_{30}$ |
|---|---|---|
| 11 | 85.5 | 253 |
| 12 | 86.5 | 256 |
| 13 | 85.2 | 251 |
| 14 | 85.9 | 254 |

The work-rate (amount of ethylene oxide produced per unit time) represented by this performance in combination with the selectivities attained above is very good.

The dielectric constants of the solvents used above are shown in Table 3.

TABLE 3

| SOLVENT % w/w COMPOSITION | | | | DIELECTRIC CONSTANT |
|---|---|---|---|---|
| Methanol | 2-ethyl hexanol | Toluene | White Spirit | |
| 100 | | | | 32.6 |
| | 0.05 | | 99.95 | 2.0 |
| | 1.3 | | 98.7 | 2.1 |
| | 0.4 | 99.6 | | 2.4 |
| | 0.4 | | 99.6 | 2.1 |
| | 0 | 100 | | 2.4 |
| | 0 | | 100 | 2.1 |

White spirit is a mixture of hydrocarbons according to BS 245 (1956)

Example 10

In this example, catalyst support pellets comprising α-alumina containing 460 ppm w/w compounds of silicon expressed as silicon, 88 ppm w/w sodium compounds expressed as sodium, 19 ppm w/w potassium compounds expressed as potassium, 360 ppm w/w iron compounds expressed as iron and 375 ppm w/w of calcium compounds expressed as calcium in the form of cylinders 8mm diameter and 7-9 mm long pierced by a single hole 2-3 mm diameter were used. The mean pore diameter of the porous alumina was 1.6 microns, its water porosity was 0.42 mols per g and its surface area was 0.72 m$^2$ per g. The pellets were uniformly coated with silver metal particles as described below.

Silver nitrate (4,309 g) was dissolved at 70° C. into distilled water (901 ml) and the resulting solution cooled to 50° C. Monoisopropylamine (4,800 ml) was slowly added to this solution whilst stirring and cooling. The addition of the amine was sufficiently slow to avoid undue temperature rises caused by the exothermic process of complex formation between the amine and the silver salt. The temperature was maintained in the range 40 to 60° C. The resulting clear solution was cooled to room temperature.

Support pellets (4,150 g) were evacuated before the addition of the solution of silver nitrate/monoisopropylamine complex (5.1). After contacting the solution for 30 minutes, the impregnated pellets were separated from the residual solution and drained.

The support pellets, wet with the impregnated complex solution, were charged to a perforated basket which was then loaded into a reactor. The impregnated support was heated in a stream of hot nitrogen gas, the temperature of the reactor being set at 100° C. and subsequently gradually increased from 100° C. to 300° C. over a period of 18 hours. The impregnated complex decomposed to leave particulate silver evenly dispersed on the surface of the porousα-alumina pellets. The pellets also contained a residue of substances containing carbon and nitrogen.

The silver-coated pellets were contacted with hot water in the temperature range 90 to 100° C. for 16 hours, cooled, drained and dried in a stream of hot water in the temperature range 90 to 100° C. for 16 hours, cooled, drained and dried in a stream of hot nitrogen. The washed silver-coated pellets were subsequently contacted with hot air in a process which began by passing a stream of 5% air-in-nitrogen over the pellets heated at 150° C. Subsequently the air content of the gas stream and the reactor temperature were both gradually increased to 100% and 300° C., respectively. The rate of both changes were sufficiently slow as to avoid uncontrolled rises in temperature of the pellets due to the exothermicity of the process. On reaching 300° C., the pellets were contacted with the air-stream for a further 14 hours and then allowed to cool.

The resulting silver-coated pellets, now substantially free of the residues of the anaerobic decomposition process were again contacted with hot water in the temperature range 90 to 100° C. for 16 hours, then cooled, drained and dried by contacting with a stream of hot nitrogen. The product was a catalyst precursor and was characterised as a substantially clean, dry dispersion of silver particles even coated on the surfaces, both internal and external, of the porous α-alumina pellets.

Portions of the catalyst precursor (water absorption, 0.35 ml per g;) were impregnated with solutions of potassium 2-ethyl hexanoate dissolved in various solvents. The catalyst precursor was contacted with the potassium solution for 16 hrs, after which the pellets were separated from the residual solution, drained and dried.

Catalyst 15 was prepared by contacting the catalyst precursor (4.34g) with potassium 2-ethyl hexanoate (6.73 mls; 2400 grams potassium per 1000 litres) dissolved in n-decanol. As evaluated from the absorbency and the concentration of the potassium solution originally added to the pellets, the catalyst would have been expected to contain 750 ppm w/w of potassium. Catalyst 16 was prepared in a similar manner to catalyst 15 with the exception that the solvent of the potassium solution was iso-decanol Catalyst 17 was similar to catalysts 16, except that the potassium content of the solution was 1600g/1000 litres. On the aforesaid basis the catalyst would have been expected to contain 500 ppm w/w of potassium.

Catalyst 18 was similar to catalysts 15 and 18 except potassium 2-ethyl hexanoate was dissolved in n-dodecanol.

Catalysts 15, 16, 17 and 18 were tested as in Example 1. The average results for catalysts 15 to 18 at from 3 to 8 days testing are presented in Table 5.

TABLE 5

| Catalyst | $S_{30}$ | $T_{30}$ |
|---|---|---|
| 15 | 83.7 | 245 |
| 16 | 85.0 | 245 |
| 17 | 83.7 | 241 |
| 18 | 85.6 | 246 |

The dielectric constants of the solvents used above are shown in Table 4.

TABLE 4

| SOLVENT % w/w COMPOSITION | | | DIELECTRIC CONSTANT |
|---|---|---|---|
| n-decanol | iso decanol | n dodecanol | |
| 100 | 0 | 0 | 8.1 |
| 0 | 100 | 0 | 6.8 |
| 0 | 0 | 100 | 3.9 |

I claim:

1. A process of improving the performance of a catalyst for the production of alkylene oxides by the reaction of the corresponding alkene with oxygen which comprises silver supported on an α-alumina support which comprises introducing an alkali metal selected from lithium, sodium, rubidium, and/or potassium to the catalyst in a ratio of one part chemically absorbed to at most three parts physically deposited, by contacting the catalyst with a solution or colloidal solution of a compound of lithium, sodium, rubidium, and/or potassium in a solvent which has a dielectric constant of at most 8 at 20° C.

2. A process as claimed in claim 1 in which the alkali metal is potassium.

3. A process as claimed in claim 2 in which the dielectric constant of the solvent is at most 5 at 20° C.

4. A process as claimed in claim 3 in which the solvent comprises one or more hydrocarbons and a small quantity of an alcohol, polyether or acid having 5 to 20 carboin atoms per-OH group to assist solubility of the alkali metal compound.

5. A process of claimed in claim 3 in which the alkali metal compound is a salt of a carboxylic acid having 5 to 20 carbon atoms per —COOH group.

6. A process as claimed in claim 1 in which 0.001 to 0.03 gram equivalents of alkali metal are chemically absorbed per kilogram of the total catalyst and in which more chemically absorbed than physically deposited alkali metal is introduced.

7. A process as claimed in claim 2 in which the catalyst which is improved comprises 5 to 15% silver by weight supported on a support of surface area 0.05 to 10m²/g, and has an apparent porosity as measured by the mercury absorption method of at least 20% and mean pore diameters of 0.1 to 20 microns, which is substantially free from organic matter.

8. A process as claimed in claim 7 in which the catalyst which is improved is washed with water and/or oxidised with molecular oxygen before the introduction of the alkali metal according to claim 1.

* * * * *